US006287555B1

(12) United States Patent
Gill et al.

(10) Patent No.: US 6,287,555 B1
(45) Date of Patent: Sep. 11, 2001

(54) METHOD AND VACCINE FOR PREVENTION OF OVER-PRODUCTION OF ACID IN THE RUMEN OR GUT OF ANIMALS

(75) Inventors: Harsharnjit Singh Gill, Palmerston North (NZ); Ronald Alfred Leng, Yandina Creek (AU); Quan Shu, Palmerston North (NZ)

(73) Assignee: The University of New England, Armidale (AU)

( * ) Notice: Subject to any disclaimer, the term of this patent is extended or adjusted under 35 U.S.C. 154(b) by 0 days.

(21) Appl. No.: 08/913,373

(22) PCT Filed: Mar. 14, 1996

(86) PCT No.: PCT/AU96/00143

§ 371 Date: May 13, 1998

§ 102(e) Date: May 13, 1998

(87) PCT Pub. No.: WO96/28177

PCT Pub. Date: Sep. 19, 1996

(30) Foreign Application Priority Data

Mar. 14, 1995 (AU) .................................................. PN 1754

(51) Int. Cl.⁷ ........................... A01N 63/00; A61K 39/00; A61K 39/02; A61K 39/09
(52) U.S. Cl. .................. 424/93.1; 424/93.44; 424/184.1; 424/234.1; 424/244.1
(58) Field of Search ............................... 424/93.1, 93.44, 424/184.1, 234.1, 244.1

(56) References Cited

FOREIGN PATENT DOCUMENTS

| A-41587/93 | 6/1993 | (AU) . |
| A-57915/86 | 5/1998 | (AU) . |
| WO 95/33046 | 12/1995 | (WO) . |

OTHER PUBLICATIONS

Plotkin et al (*Vaccines* published by W.B. Saunders Co., Philadelphia, p. 571), 1988.*
Pazur et al (Analytical Biochemistry vol. 126 pp. 285–294), 1982.*
Alderere (Genitourin. Med. vol. 64, pp. 118–123), 1988.*
Shu, Quan, (1997) *Immunization Against Lactic Acidosis in Sheep and Cattle*,Chapter 10, pp. 138–145, Thesis submitted for a Doctor of Philosophy of the University of New England.
Owens et al., (1998) *J. Anim. Sci.*, vol. 76, pp. 275–286.
Nagaraja et al., (1998) *Veterinary Clinics of North America: Food Animal Practice*, vol. 14, No. 2, p. 257.
*Clinical Aspects of Immunology*, (1968) Eds. PGH Bell & RRA Coombs. Blackwell Scientific Publications pp.: 293–294.
Adorini et al., (1992) *Immunodominance*, In: Encyclopedia of Immunology, (I.M. Ry , Ed., Economic Press, London, pp. 808–809.
Herbert, (1974) *Veterinary Immunology*, (Blackwell Scientific Publications, Oxford U.K.), pp. 197–202.
Hobart and McDonnell, (1975) *The Immune System—A Course on the Molecular and Cellular Basis of Immunity*, (Blackwell Scientific Publications, Oxford U.K.), pp. 165–178.
Sinigaglia, (1992) *Antigenic Competition*l , in: Encyclopedia of Immunology , (I.M. Roy, Ed., Academic Press, London), pp. 123–126.
Rimemelzwaan and Osterhaus, (1997) *The Immune Response*, in: Veterinary Vaccinology, p. 58.

* cited by examiner

Primary Examiner—Mark Navarro
(74) Attorney, Agent, or Firm—McDonnell Boehnen Hulbert & Berghoff

(57) ABSTRACT

The present invention is directed to a method of preventing the over-production of acid in an animal comprising administering to the animal a vaccine including an acid producing microorganism and/or antigenic fragment or fragments thereof effective to prevent the over-production of acid in the animal. The vaccine includes lactic acid producing microorganisms obtainable from the normal gut flora of an animal. In particular the vaccine includes *Streptococcus bovis* and/or *Lactobacillus* spp.

8 Claims, No Drawings

METHOD AND VACCINE FOR PREVENTION OF OVER-PRODUCTION OF ACID IN THE RUMEN OR GUT OF ANIMALS

The present invention relates to methods and compositions for the prevention of the over production of acid in an animal, and in particular is directed to a method and composition for the prevention of acidosis in a ruminant

BACKGROUND ART

The over production of acid in an animal by microorganisms can cause acidosis which is defined as a condition of pathologically high acidity of the blood. In ruminants the term is expanded to include acidic conditions in the rumen.

Acidosis in ruminants is a frequently observed acute condition that is also known as "grain engorgement", "grain overload" or "acute indigestion". It occurs when the diet of ruminants is changed abruptly to contain large amounts of starch or other rapidly fermentable carbohydrates. A high incidence of acidosis is associated with feed lot livestock when their diet is rapidly changed from a forage-based ration to a grain-based ration. The rumnen undergoes a marked decrease of pH initiated by an increased rate of production of acids during the fermentative digestion of grains. The acids are then absorbed into the blood stream resulting in many of the clinical symptoms of acidosis. In many instances, *Streptococcus bovis* becomes the dominant bacteria as pH drops resulting in the production of lactic acid which is then absorbed from the rumen. The growth and metabolic activity of this and other acid producing organisms further lowers rumen pH. The condition of acidosis can be acute, posing a life-threatening situation, or chronic (sub-acute), resulting in reduced feed intake and weight gain.

Gross symptoms of acidosis include reduction or cessation of feed consumption (anorexia), loose faeces or diarrhoea, a listless, depressed or distressed appearance, founder or sore feet and death. Other symptoms that can be measured or observed after the onset of acidosis include decreased rate of grain and feed efficiency, high incidence of abscessed livers at slaughter, ruminates in slaughtered or dead animals, altered blood metabolic profile and incidence of polioencephalomalacia. Abscessed livers are condemned at slaughter, are an economic loss to the meat processor and ultimately adversely affect the market price of livestock. In particular, cattle with badly abscessed livers do not gain weight as rapidly or efficiently as unaffected animals.

Non-ruminant animals such as horses and the like are also susceptible to acidosis. The increasing popularity of horse related sports and activities has also led to an increase in the total incidence of acidosis in these animals. Horses are often housed in close quarters and are routinely grain fed when other fodder is unavailable, leading to the increased risk of acidosis.

In order to minimise or prevent the incidence of acidosis in livestock, current practices centre around management techniques, including introducing grain slowly to the diet of the animals. This involves close monitoring of daily feed intake, checking the animals condition and providing fresh feed and water daily. This method is time-consuming as rations must be mixed and prepared and the animals must be monitored carefully for the incidence of acidosis.

Recent studies have demonstrated that inclusion of antibiotics including Virginiamycin in the diet removes the need for a gradual introduction to grain feeding in feedlot animals or animals fed on grain in a drought. The inclusion of antibiotics also reduces the possibility of animal losses. The widespread use of antibiotics in the livestock industry however is not considered acceptable as the potential for emergence of drug-resistant microbial strains is high. In addition, there is an attendant risk to public health through antibiotic residues in animal products. The presence of antibiotics in animal products may also endanger export earnings as many countries prohibit the importation of animal products containing antibiotics.

Another strategy to reduce the incidence of abscessed livers and the effects of acidosis is to include dietary buffers or neutrlisers (bicarbonates, hydroxides, silicates) in feed. These additives have beneficial effects during initial phase of adaptation to high carbohydrate containing diets during the first few weeks of feeding. These additives do not, however, provide consistent benefit in feedlot performance over the entire finishing period. The levels used, that are initially beneficial, may cause overall performance to be inferior to that obtained without additives.

Acidosis can also be a major problem during drought conditions where grain is often the only food source available for livestock. To place animals on a pure grain diet under these harsh conditions can cause a high incidence of acidosis often leading to death. There is a real need to have an economical and efficient means of protecting animals from the incidence of the over production of acid and acidosis.

The present inventors have developed an alternative strategy for the prevention of the over production of acid and acidosis in animals.

DISCLOSURE OF THE INVENTION

Accordingly, in a first aspect the present invention consists in a method of preventing the over production of acid in an animal comprising administering to the animal a vaccine including an acid producing microorganism and/or antigenic fragment or fragments thereof effective to prevent the over production of acid in the animal.

In a preferred embodiment of the first aspect of the present invention, the over production of acid is the over production of lactic acid.

In a further preferred embodiment of the first aspect, the acid producing microorganism forms part of the normal gut flora of an animal. Preferably the microorganism is a lactic acid producing microorganism, More preferably the microorganism is *Streptococcus bovis* or Lactobacillus spp and most preferably both *S. bovis* and Lactobacillus spp. The preferred *S. bovis* strain is Sb-5.

In a still further preferred embodiment of the first aspect, the animal is a monogastric animal or a ruminant and more preferably the monogastric animal is a horse and the ruminant is selected from, the group consisting of sheep, cattle and goats.

Administration of the vaccine may be subcutaneous, intramuscular, intravenous, oral or interperitoneal. It will be appreciated by one skilled in the art, however, that any administration would be suitable.

The method according to the first aspect of the present invention is suitable to prevent the over production of acid which causes conditions in an animal including acidosis, lactic acidosis, grain engorgement, grain overload, carbohydrate overload, founder, laminitis, acute indigestion or any other condition.

In a second aspect, the present invention consists in a vaccine effective to prevent the over production of acid in an animal comprising an acid producing microorganism and/or antigenic fragment or fragments thereof.

In preferred embodiment of the second aspect of the present invention, the acid producing microorganism forms part of the normal gut flora of an animal. Preferably the microorganism is a lactic acid producing microorganism. More preferably the microorgansm is *S. bovis* or Lactobacillus spp and most preferably both *S. bovis* and Lactobacillus spp. The preferred *S. bovis* strain is Sb-5.

The vaccine may comprise live cells, attenuated cells, killed whole cells, cell lysate, crude antigen mixture or purified antigen or antigens from the microorganism. The vaccine may also contain pharmaceutically acceptable adjuvants, carriers or excipients known to the art.

In a third aspect the present invention consists in the microorganism *S. bovis* (strain Sb-5), deposited with the Australian Government Analytical Laboratories (AGAL) on Mar. 8, 1994 and given accession number N94/8255.

In order that the nature of the present invention may be more clearly understood, preferred forms thereof will be described with reference to the following examples.

MODES FOR CARRYING OUT THE INVENTION

EXAMPLE 1

Development of a Vaccine for the Prevention of Acidosis Sheep

Eighteen-month-old, fine wool Merino wethers were used for vaccination studies.

Bacteria

*Streptococcus bovis* (strain Sb-5), isolated from the rumen content of cattle fed on grain-based diet was used. The inoculum for vaccination was prepared by sub-culturing *S. bovis* in a specially developed medium (RSY medium) for 6 hours at 38° C. Both live and killed *S. bovis* were used for immuinsation.

| RSY-1 medium: | | |
|---|---|---|
| Yeast extract | 0.2% | (1.0 g) |
| Soluble starch | 0.5% | (2.5 g) |
| NaHCO$_3$ | 0.5% | (2.5 g) |
| Salt sol. A | 82.5 ml | |
| Salt sol. B | 82.5 ml | |
| Rumen Fluid | 165 ml | |
| Distilled water | 170 ml | |

| Salt solution A | | Salt solution B | |
|---|---|---|---|
| 0.3% | KH$_2$PO$_4$ | 0.3% | K$_2$HPO$_4$ |
| 0.6% | NaCl | | |
| 0.3% | (NH$_4$)$_2$SO$_4$ | | |
| 0.03% | CaCl$_2$ | | |
| 0.03% | MgSO$_4$ | | |

Preparation of *S. bovis* Vaccine

1. Culture *S. bovis* for 6 h in RSY-1 medium.
2. Harvest bacteria by centrifuging at 3.000 g for 25 mins at 4° C., and then centrifuging at 10,000 g for 15 mins.
3. Discard supernatant and collect pellet.
4. For live vaccine, wash bacteria 2 times in PBS by centrifugation and adjust bacterial counts to $10^{10}$ *S. bovis*/ml.
5. For killed vaccine, suspend bacterial pellet in equal volume of phosphate buffered saline (pH7.4) (PBS) and then add 0.48% formaldehyde.

Allow to stand overnight at 4° C. Wash bacterial cells in PBS and then adjust to $10^{10}$ cells/ml of *S. bovis*/ml by direct microscopic count (Gilstrap M. Kleyn J G, Eugene W N, (1983). In "Experiments in Microbiology", Saunders College Publishing, The Dryden Press, pp:87–100 and Ogimoto K and Imai S. (1980). In "Atlas of Rumen Microbiology", Japan Scientific Societies Press, Tokyo, pp 159–170).

For vaccination, *S. bovis* suspension (live or killed) was treated as follows:

a) FCA and FIA (Freund's complete adjuvant and Freund's incomplete adjuvant, respectively)—1 ml *S. bovis* suspension was emulsified with an equal volume of FCA or FIA.

b) Quil A—the *S. bovis* suspension was vortexed for 2 min with an equal volume of 1 mg/ml Quil A in PBS.

c) Live or killed *S. bovis* (without any adjuvant).

TABLE 1

Vaccination Protocol. Vaccines were prepared using $10^{10}$ killed or live *S. bovis* organisms in 1 ml sterile PBS, emulsified in 1 ml of FCA. FIA. or mixed with 1 mg of Quil A in 1 ml PBS or 1 ml PBS only. The vaccines were administered in 2 ml volume intramuscularly.

| | Treatment (Group) | | | | | |
|---|---|---|---|---|---|---|
| Time (week) | 1 (n = 5) | 2 (n = 5) | 3 (n = 5) | 4 (n = 5) | 5 (n = 5) | 6 (n = 5) |
| 0 | Sb$^1$ + FCA | Sb$^2$ + FCA | Sb$^1$ + Quil A | Sb$^1$ | Sb$^2$ | — |
| 4 | Sb$^1$ + FIA | Sb$^2$ + FIA | Sb$^1$ + Quil A | SB$^1$ | Sb$^2$ | — |
| 6 | Sb$^1$ + FIA | Sb$^2$ + FIA | Sb$^1$ + Quil A | Sb$^1$ | Sb$^2$ | — |
| 8 | Sb$^1$ + FIA | Sb$^2$ + FIA | Sb$^1$ + Quil A | Sb$^1$ | Sb$^2$ | — |

Sb: *S bovis* strain Sb-5: Sb$^1$: $10^{10}$ killed Sb-5 suspension: Sb$^2$: $10^{10}$ live Sb-5 suspension; FCA. Freund's complete adjuvant: FIA. Freund's incomplete adjuvant.

To examine the effectiveness of vaccination in protecting sheep against acidosis, sheep were introduced to wheat grain after overnight fasting. On the challenge day, all sheep received 1400 g of wheat. After 8 h. all animals had eaten 1400 g of wheat.

Protection was assessed by measuring feed intake, severity of diarrhoea and change in rumen pH. The results are shown in Table 2. All unvaccinated sheep (5/5 in Group 6) showed signs of severe acidosis—runny diarrhoea, decreased rumen pH (4.5–5.3) and complete loss of appetite. Sheep in groups 1, 3 and 4 suffered moderate to severe acidosis. Moderate protection was observed in animals in group 5. Three animals showed no clinical sign of acidosis and kept on feeding normally. Two animals were moderately affected. All sheep in group 2 were protected against acidosis. Slightly softer faeces were observed in one animal only. All animals showed normal appetite and kept on feeding normally.

The antibody responses are summarised in Table 3 and show very high concentrations in sheep vaccinated using Freund's complete or incomplete adjuvants and lower, but still elevated levels when QuilA was used as the adjuvant.

TABLE 2

Responses of Vaccinated and Unvaccinated (Control) Sheep to Grain Feeding; (vaccination protocol is detailed in Table 1).

| Group (No. animals) | Feed intake | General Condition | Diarrhoea | Rumen pH |
|---|---|---|---|---|
| 1 (5) | Stopped eating after day 1 | Very sick (withdrawn from the experiment after 48 h) | Mild (1/5) Severe (4/5) | 5.2–5.8 |
| 2 (5) | Unaffected (normal). | Healthy (5/5) | One animal had softer faeces on day 5 | >6.0 |
| 3 (5) | Stopped eating after day 1 | Very sick (withdrawn from the experiment after 48 h) | Moderate (2/5) Severe (3/5) | 5.2–5.8 |
| 4 (5) | Stopped eating after day 1 | Very sick (withdrawn from the experiment after 48 h) | Moderate (2/5) Severe (3/5) | 5.1–5.8 |
| 5 (5) | Unaffected (3/5). and (2/5) stopped eating after 48 h | Healthy On day 3 two sheep appeared distressed and listless | None (3/5). Moderate (1/5). Severe (1/5) | >5.6 |
| 6 (5) control | Stopped eating after day 1 | Very sick (withdrawn from the experiment after 48 h) | Moderate (1/5) Severe (4/5) | 4.5–5.3 |

TABLE 3

Antibody Response (antibody titre × 1,000) to *S bovis* in Serum Sample of Sheep in Example 1. The vaccination treatments are described in Table 1

| | Group | | | | | |
|---|---|---|---|---|---|---|
| | 1 | 2 | 3 | 4 | 5 | 0 |
| Before immunisation | 2 | 2 | 2 | 2 | 2 | 2 |
| After immunisation | 3200 | 6400 | 800 | 50 | 50 | 2 |

EXAMPLE 2

Immunisation Against Lactic Acidosis in Sheep

Forty-three Merino lambs (approximately 6 months old, live weight 22.4+2.7 kg) were randomly allocated to three treatment groups (Table 4).

TABLE 4

Vaccination Protocol for Lambs in Experiment Described in Example 2.

| Time (week) | 1 (n = 15) | Treatment (Group) 2 (n + 13) | 3 (n = 15) |
|---|---|---|---|
| 0 | Sb + FCA[a] | Sb + FCA[b] | — |
| 4 | Sb + FIA[a] | Sb + FIA[a] | — |
| 6 | Sb + FIA[c] | Sb + FIA[c] | — |

TABLE 4-continued

Vaccination Protocol for Lambs in Experiment Described in Example 2.

| Time (week) | 1 (n = 15) | Treatment (Group) 2 (n + 13) | 3 (n = 15) |
|---|---|---|---|
| 9 | Sb + FIA[c] | Sb + FIA[c] | — |
| 10 | Grain challenge* | Grain challenge | Grain challenge |

Sb: $10^{10}$ live Sb-5 suspension: a: intramuscular; b: intraperiloneal; c: 50% orally (killed Sb-5 without adjuvant) and 50% (live Sb-5 with FCA) intramuscularly; *: wheat 600 g + 200 g lucerne chalf/day for 3 weeks.

*Streptococcus bovis* strain Sb-5 was prepared as previously by culturing in RSY-II medium for 6 to 10 h at 38.5° C. The composition of the RSY medium as described above was modified to include 1.0 g starch was used instead of 0.5 g and 0.5 g of yeast extract was used instead of 0.2. The bacteria were harvested by centrifugation (10,000 g 25 minutes) at 4° C. washed 3 times with sterile PBS and re-suspended in sterile PBS. The concentration of bacterial cells in the suspension was determined by direct microscopic count and adjusted to $1 \times 10^{10}$ cells/ml. The final solution was adjusted to pH 6.5 and aliquots were stored at −80° C. and thawed in a cold water bath immediately before use. The suspension was mixed vigorously for 10 minutes before use in order to break possible cell clusters.

Lambs in groups 1 and 2 were vaccinated against *S. bovis* whereas lambs in group 3 served as unvaccinated controls. Seven days after the last immunisation, all lambs were introduced to a grain-based diet. Feed intake, changes in rumen pH, incidence and severity of diarrhoea, and *S. bovis*-specific antibody levels in serum, saliva and rumen fluid were monitored to determine the protective effect of vaccination against lactic acidosis.

Both intraperitoneal and intramuscular immnunisations induced high levels of anti-*S. bovis* antibodies in serum (see Table 5), saliva and rumen fluid; specific antibodies belonged to both IgG and IgA isotypes. Intraperitoneal immuisation induced a markedly higher IgA response in saliva compared with intramuscular immunisation.

TABLE 5

Antibody Concentration (units/ml) in Serum Samples of Sheep. The actual antibody data are shown in the table. P values were estimated using data which were log transformed before analysis of ANOVA. Primary vaccination was given on day 0 and boosters were given on day 28, 46, and 67.

| Time | 1 (n = 15) | | 2 (n = 13) | | 3 (n = 15) | | |
|---|---|---|---|---|---|---|---|
| (days) | Mean | SE | Mean | SE | Mean | SE | P |
| 0 | 1.5 | 0.4 | 1.4 | 0.4 | 0.9 | 0.1 | 0.36 |
| 28 | 2.4 | 0.5 | 1.4 | 0.5 | 0.5 | 0.1 | <0.01 |
| 46 | 15.5 | 1.8 | 13.5 | 3.9 | 0.5 | 0.1 | <0.01 |
| 67 | 159.4 | 33.9 | 77.4 | 13.7 | 0.9 | 0.1 | <0.01 |
| 75 | 233.6 | 60.8 | 61.4 | 13.1 | 1.1 | 0.2 | <0.01 |
| 87 | 137.9 | 10.2 | 67.6 | 12.1 | 0.6 | 0.1 | <0.01 |

Immnunised lambs exhibited significantly higher feed intake and rumen pH at all observation times (see Table 6). The incidence and seventy of diarrhoea were also significantly lower in immunised lambs than those of control lambs (immunised lambs 0 to +, controls ++ to ++++).

Levels of lactic acid (D- and L-isomers) in blood plasma and rumen fluid following grain challenge were markedly higher in control lambs than those of vaccinated lambs. After grain challenge, there was a decrease in the live weight of control lambs (−50 g/day) but a steady increase in the live weight of immunised animals (+45 g/day).

All vaccinated animals showed significant protection against lactic acidosis; intraperitoneal and intramuscular immunisations conferred similar levels of protection. Protection was associated with salivary and rumen antibody levels.

the other (control) group received no vaccination. The vaccinated group received vaccination injections during weeks 1, 4, 6, 8 and 10 of the experiment. During week 12 animals were challenged with grain. The grain challenge consisted of changing the diet suddenly from 10 kg lucerne chaff/day to 6 (kg concentrate/day (90% rolled wheat +5% roughage +1% urea +1% limestone, 2.5% cottonseed +0.5% salt).

Preparation of Vaccine

*Streptococcus bovis* strain Sb-5 suspension was made as described in Example 2 Lactobacillus spp LB-27 was isolated from the rumen content of a cattle fed on grain-based diet. LB-27 was cultured in LFM medium (described below) for 18 to 24 hours at 38.5° C. The bacteria were harvested by centrifugation (4.700 g 25 minutes) at 4° C., washed 3 times with sterile phosphate-buffered saline pH 7.4 (PBS) and re-suspended in sterile PBS. The concentration of bacterial cells in the suspension was determined by direct microscopic count and adjusted to $2\times10^{10}$ cells/ml. aliquoted and stored at −80° C. until use.

Lactobacillus LB-27 was cultured in LFM medium for 18 to 24 hours at 38.5° C. The bacteria were harvested by centrifugation (4,700 g 25 minutes) at 4° C. washed 3 times with sterile phosphate-buffered saline pH7.4 (PBS) and resuspended in sterile PBS. The concentration of bacterial cells in the suspension was determined by direct microscopic count and adjusted to $2\times10^{10}$ cells/ml. Alliquots were stored at −80° C. until use.

Stored bacterial preparations (BP: Sb-5 and, LB-27 suspensions kept at −80°) were thawed at cold water bath immediately before use. Mixed vigorously for 10 minutes to break the possible cell clusters.

Vaccine Preparation

The vaccine were prepared containing the BP ($3\times10^{10}$ live *S. bovis* Sb-5 and $1\times10^{10}$ LB-27) in 2.5 ml of BP emulsified with an equal volume of Freund's complete adjuvant. All vaccinations were given intramuscularly.

The grain challenge consisted of changing the diet suddenly from 10 kg lucerne chaff/day to 6 kg concentrate/day (90% rolled wheat +5% roughage +1% urea +1% limestone, 2.5% cottonseed+0.5% salt).

Protection against acidosis was assessed by measuring feed intake, severity of diarrhoea, changes in rumen and faecal pH.

TABLE 6

Responses of Vaccinated and Unvaccinated (Control) Sheep to Grain Feeding.

| Group No. | Feed Intake | General Condition | Diarrhoea |
|---|---|---|---|
| 1 (vac. i.m.) | Unaffected (9/15) Intake reduced by 25% (6/15) | Healthy | Mild (+) diarrhoea (5/15) |
| 2 (vac. i.p.) | Unaffected (9/13) Intake reduced by 25% (4/13) | Healthy | Mild (+) diarrhoea (3/13) |
| 3 (control) | Unaffected (4/15) Intake reduced by 70% (11/15) | Healthy 2/15. very sick (5/15). distressed and listless (8/15) | Mild (+) diarrhoea (2/15). Moderate (++) diarrhoea (3/15). severe (+++) diarrhoea (10/15) |

EXAMPLE 3

Immunisation Against Lactic Acidosis in Cattle

Ten cattle were randomly allocated to two treatment groups. One group was vaccinated as described below and Vaccination elicited a high level of antibody response to *S. bovis* and Lactobacillus spp in saliva, rumen blood and serum. Concentrations of antibodies in blood are summarised in Table 7.

TABLE 7

IgG Concentrations (units/ml) in Serum Samples taken from Cattle Prior to and following Vaccination against *S. bovis* and *Lactobacillus spp* using Freund's Complete Adjuvant (Example 3). Primary immunisation was given on day −91 and boosters were given on days −61, −47, −32, −18. Means and standard errors in this table are shown as actual values but the P value was determined using $\log_{10}$ transformed data.

| Time (days) | Immunisation Mean | SE | Control Mean | SE | P |
|---|---|---|---|---|---|
| Antibody IgG to *Streptococcus bovis* | | | | | |
| −91 | 2.2 | 0.7 | 1.9 | 0.9 | 0.62 |
| −61 | 8.1 | 4.4 | 2.8 | 0.4 | 0.23 |
| −47 | 24.6 | 11.2 | 2.8 | 0.4 | <0.01 |
| −32 | 93.8 | 38.2 | 1.7 | 0.4 | <0.01 |
| −18 | 56.0 | 11.4 | 3.2 | 1.2 | <0.01 |
| −0.666 | 199.4 | 81.1 | 5.5 | 0.6 | <0.01 |
| 0.333 | 191.3 | 78.3 | 4.4 | 0.4 | <0.01 |
| 0.666 | 170.2 | 60.2 | 5.3 | 0.8 | <0.01 |
| 1 | 146.4 | 47.3 | 5 | 0.6 | <0.01 |
| 2 | 166.8 | 65.8 | 4.4 | 0.8 | <0.01 |
| 3 | 140.7 | 47.1 | 5.1 | 1.1 | <0.01 |
| 6 | 139.8 | 45.8 | 5.1 | 0.7 | <0.01 |
| 9 | 118.4 | 42.7 | 4.7 | 0.6 | <0.01 |
| 30 | 76.3 | 30.1 | 5.2 | 0.9 | <0.01 |
| Antibody IgG to *Lactobacillus spp* | | | | | |
| −91 | 29.1 | 10.5 | 30.3 | 4.6 | 0.6 |
| −61 | 14.5 | 5.3 | 20.2 | 1.6 | 0.19 |
| −47 | 24.0 | 6.3 | 19.8 | 4.6 | 0.79 |
| −32 | 77.4 | 11.9 | 12.7 | 3.3 | <0.01 |
| −18 | 151.9 | 19.0 | 20.0 | 3.6 | <0.01 |
| −0.666 | 154.4 | 31.5 | 18.2 | 2.6 | <0.01 |
| 0.333 | 147.3 | 48.2 | 16.1 | 2.7 | <0.01 |
| 0.666 | 122.9 | 30.2 | 17.8 | 2.7 | <0.01 |
| 1 | 126.9 | 28.4 | 16.4 | 2.7 | <0.01 |
| 2 | 122.1 | 27.4 | 18.6 | 4.8 | <0.01 |
| 3 | 109.4 | 17.3 | 22.0 | 10.8 | <0.05 |
| 6 | 94.4 | 14.3 | 15.2 | 1.8 | <0.01 |
| 9 | 85.0 | 12.5 | 17.6 | 2.4 | <0.01 |
| 30 | 52.6 | 10.4 | 15.4 | 2.0 | <0.01 |

Primary immunisation was given on day −91 and boosters were given on days −61, −47, −32, −18. Prior to statistical analysis values were log transformed and means in this table are shown as log (base 10) values.

The responses of cattle to the grain challenge are summarised in Table 7. Three of the five cattle showed solid protection against lactic acidosis. Two animals showed moderate protection. Four of the five control (unvaccinated) cattle showed signs of severe acidosis—decrease in rumen and faecal pH, loss of appetite and severe diarrhoea (+++). Twenty-four hours after grain challenge, three animals were withdrawn from the experiment.

Protection was associated with high levels of anti-*S. bovis* and *Lactobacillus spp* antibodies in saliva, rumen fluid and serum. Together these results show a significant reduction in problems associated with acidosis in response to immunisation against *S. bovis* and *Lactobacillus spp*.

TABLE 8

Responses of Vaccinated and Control Cattle to Grain Feeding (Example 3).

| Group No. | Feed Intake | General Condition | Diarrhoea | Rumen pH |
|---|---|---|---|---|
| Vaccine | Unaffected (4/5) | Healthy (4/5). One animal withdrawn from the experiment after 48 hours | Mild (3/5). moderate (1/5). severe (1/5) | >5.2 (4/5) <5.0 (1/5) |
| Control | Unaffected (2/5) | Healthy (2/5). Two animals withdrawn from the experiment after 24 hours and one after 48 hours | Mild (1/5). moderate (1/5). severe (3/5) | >5.2 (2/5) <5.0 (3/5) |

EXAMPLE 4

Immunisation Against Lactic Acid Bacteria in Cattle Using Various Adjuvants

Twenty four cattle were used in an experiment to investigate vaccination procedures with different adjuvants. Previous studies by the present inventors have shown that vaccination against lactic acid producing bacteria can alleviate the consequences of excessive levels of readily fermentable carbohydrate. These studies have been based on the use of Freund's Complete Adjuvant (FCA) which is not acceptable for routine use or commercial application. The current study was designed to investigate the extent and duration of antibody accumulation in cattle following vaccination against lactic acid producing bacteria.

Experimental Procedures

There were 5 treatment groups as follows:

(i) Control group receiving no vaccination (n=4);

(ii) Freund's Complete Adjuvant (FCA) for the primary vaccination and Freund's incomplete adjuvant (FIA) for the booster (N=5);

(iii) QuilA as the adjuvant for both primary an secondary injections (n=5);

(iv) DEAE-Dextran as the adjuvant for both primary an secondary injections (n=5): and (v) Alum as the adjuvant for both primary an secondary injections (n=5).

The animals were introduced to the feedlot diet by gradually increasing the concentration of grain and decreasing the amount of hay over a period of three weeks. The primary immunising injection was administered during week four and the booster injection was given during week 8. Both injections were intramuscular into the neck.

Preparation of Vaccines

All vaccines consisted of the same bacterial preparation combined with a different adjuvant. The bacterial preparation (BP) was prepared as follows:

BP *Streptococcus bovis* (Sb-5) and *Lactobacillus spp* (LB-27) had been prepared previously as described for Example 2 and 3. Each vaccine batch was prepared using 3.50 ml of LB-27 ($2 \times 10^{10}$ cells/ml) suspension and 14.00 ml ($1 \times 10^{10}$ cells/ml) of Sb-5 suspension.

FCA The two fractions of the BP were thoroughly mixed and then emulsified with an equal volume of Freund's complete adjuvant (Sigma) for the primary vaccination and with an equal volume of Freund's incomplete adjuvant (Sigma) for the booster. Each vaccination injection was 5 ml.

QuilA The two fractions of the BP were thoroughly mixed and then added to the Quil A (Superfos Biosector a/s) in the following way. After the 7.0 mg QuilA was dissolved in 17.50 ml sterile PBS, the BP was added to it in drops over a period of 5 minutes with being vigorously mixing. The mixing was continued for another 20 minutes. Each vaccination injection was 5 ml.

Dex The 14.00 ml Sb-5 suspension was centrifuged at 4° C. and 10,000 g for 20 minutes. The supernatant, 12.25 ml was removed and the pellet was re-suspended by adding 3.50 ml of LB suspension and mixing thoroughly. The concentrated BP was mixed (vortex) with 5.25 ml of 20% DEAE-Dextran (Pharmacia) solution(pH 7.5). This mixture was then emulsified with 24.5 ml of mineral oil. Each vaccination injection was 5 ml. Alum. The two fractions of the BP were thoroughly mixed and then added to Inject Alum adjuvant (Pierce) in the following way: After 8.75 ml of the Alum was mixed well with 8.75 ml sterile PBS, the BP was added to it dropwise over a period of 5 minutes with vigorous mixing. The mixing was continued for another 30 minutes. Each vaccination injection was 5 ml.

Measurements

Samples of rumen fluid were taken during weeks 3, 6, 8 and 11 of the experiment for analysis of pH. Samples taken during weeks 3, 6 and 11 were analysed to determine the population density of the major lactic acid producing organisms (*S. bovis* and Lactobacillus spp). Samples of blood were taken 6 weeks prior to the commencement of the experiment and again during weeks 3, 6, 8, 9 and 11 of the experiment for determination of IgG antibody concentrations in serum. Samples of faeces were taken during weeks 6, 8, 9, 10, 11, 12, 13 and 15 of the experiment for analysis of pH. All animals were weighed each week and animals were observed daily for any signs of ill health.

Procedure For Measuring Antibody Response

Serum Preparation

Samples of blood were collected by jugular venipuncture into Vacutainer (Brand SST Tubes for serum separation, Becton Dickinson). Serum was removed after chilling (4° C.), centrifugation at 2,000 g for 15 minutes and then stored at −20° C. prior to analysis. The serum samples were thawed and diluted to 1:16,000 before ELISA analysis.

Elisa For IgG In Serum Of Cattle

1. Coat plate with antigen ($5 \times 10^7$ cells/ml of Sb-5 or LB-27 BP suspension) in carbonate buffer 100 μl/well, incubate 4° C. for overnight;
2. Wash with PBS containing 0.5% Tween 20 (PBST) 4 times;
3. Block plate with 2% BSA (Bovine Albumin, Sigma) in PBST (150 μl/well) at 37° C. for 1 hour;
4. Wash with PBST 3 times;
5. Add samples, blanks, and standards 100 μl/well, incubate at 37° C. for 1.5 hours;
6. Wash with PBST 4 times;
7. Add conjugate: Anti Bovine ISG(Chemicon) (1:3,000 in PBSN 100 μl/well, incubate at 37° C. for 1 hour;
8. Wash with PBST 4 times;
9. Add substrate 100 μl/well, leave at room temperature for 10 min protected from light (aluminum foil wrap);
10. Stop reaction with 2N $H_2SO_4$ 50 μl/well;
11. Mix well;
12. The absorbance was read at 492 nm using a Titertek Multiskan reader (Flow Labs).

Sampling, Culture, And Counting Procedures For Lactic Acid Bacteria In Ruminal Fluid One ml of ruminal fluid was added to 9 ml of anaerobic dilution solution and mixed well. Serial dilution was used to prepare 5 samples containing $10^{-4}$, $10^{-5}$, $10^{-6}$, $10^{-7}$, and $10^{-8}$ times the original concentrations of rumen fluid. The numbers of *S. bovis* and Lactobacillus spp were measured by colony-forming units on MBA and MRS agar respectively. Media roll tubes were inoculated in triplicate with each of file and incubated at 38.5° C. for 2–3 days.

Measurement of pH

The pH of rumen fluid was measured without dilution. Samples of faeces (1 g) were diluted with 8 ml of distilled water before measuring pH.

Statistical Analysis

Results were examined by analysis of variance for statistical significance. In the case of antibody concentrations and bacterial population density data were prepared by log transformation prior to analysis of variance.

Results

The effects of vaccination on the population of *S. bovis* and Lactobacillus spp is shown in Table 9. There were significant reductions in the numbers of both *S. bovis* ($p<0.0.2$) and Lactobacillus spp ($p=0.05$), in samples of rumen fluid taken three weeks after the booster immunisation. There was also a decrease in *S. bovis* numbers in response to vaccination in samples taken two weeks after the primary vaccination.

TABLE 9

The Population Densities ($Log_{10}$ number of colony forming units/ml) of *S. bovis* and *Lactobacillus spp* in Rumen Fluid of Cattle Vaccinated against Lactic Acid Producing Bacteria (*S. bovis* and *Lactobacillus spp*) using QuilA or Dextran as Adjuvants. The primary vaccination was during week 4 and the booster was given during week 8.

| | Control | | QuilA | | Dex | | |
|---|---|---|---|---|---|---|---|
| | Mean | SE | Mean | SE | Mean | SE | P |
| *S bovis* | | | | | | | |
| Week 3 | 6.57 | 0.231 | 7.21 | 0.181 | 7.14 | 0.262 | 0.15 |
| Week 6 | 6.64 | 0.420 | NA | NA | 5.50 | 0.231 | 0.04 |
| Week 11 | 7.76 | 0.145 | 6.79 | 0.322 | 6.19 | 0.316 | 0.01 |
| *Lactobacillus spp* | | | | | | | |
| Week 3 | 7.35 | 0.478 | 7.81 | 0.294 | 7.49 | 0.151 | 0.58 |
| Week 6 | 9.21 | 0.291 | NA | NA | 9.26 | 0.227 | 0.90 |
| Week 11 | 8.53 | 0.287 | 7.55 | 0.226 | 7.99 | 0.224 | 0.05 |

The pH of the rumen fluid, and faeces is summarised in Table 10. There were no significant differences due to vaccination in the pH of the ruminal or faecal material but a trend for samples from vaccinated animals to be higher than those of the control group.

The serological antibody response to *S.bovis* and Lactobacillus spp (IgG antibody concentration) is summarised in Table 11. These data provide a significant indication of antibody production against both bacteria with all vaccine preparations two and four weeks after the primary vaccination. A more intense immunological response appears from one to 5 weeks after the booster vaccination.

TABLE 10

The pH of Rumen Fluid and Faeces Measured in Cattle Vaccinated against Lactic Acid Producing Bacteria (*S. bovis* and *Lactobacillus spp*) using a range of different adjuvants. The primary vaccination was during week 4 and the booster was given during week 8.

| Time | Control | | FCA | | QuilA | | Dex | | Alum | |
|---|---|---|---|---|---|---|---|---|---|---|
| Weeks | Mean | SE | Mean | SE | Mean | SE | Mean | SE | Mean | SE |
| Ruminal pH | | | | | | | | | | |
| 3 | 6.95 | 0.07 | 6.90 | 0.04 | 6.74 | 0.15 | 6.79 | 0.12 | 6.96 | 0.09 |
| 6 | 5.86 | 0.13 | 6.04 | 0.16 | 5.95 | 0.26 | 5.89 | 0.09 | 6.12 | 0.14 |
| 8 | 5.93 | 0.17 | 6.25 | 0.21 | 6.33 | 0.10 | 6.03 | 0.17 | 6.02 | 0.11 |
| 11 | 6.00 | 0.24 | 5.87 | 0.17 | 6.12 | 0.19 | 6.06 | 0.16 | 5.82 | 0.23 |
| Faecal pH | | | | | | | | | | |
| 6 | 6.91 | 0.15 | 7.15 | 0.07 | 7.14 | 0.11 | 7.51 | 0.28 | 7.21 | 0.05 |
| 8 | 6.76 | 0.11 | 6.48 | 0.08 | 6.83 | 0.20 | 6.83 | 0.16 | 6.77 | 0.20 |
| 9 | 6.76 | 0.19 | 7.06 | 0.34 | 7.13 | 0.13 | 6.65 | 0.15 | 6.85 | 0.21 |
| 10 | 6.78 | 0.18 | 7.21 | 0.22 | 7.00 | 0.16 | 6.92 | 0.13 | 7.05 | 0.33 |
| 11 | 6.40 | 0.12 | 6.49 | 0.06 | 6.62 | 0.14 | 6.81 | 0.13 | 6.41 | 0.14 |
| 12 | 8.65 | 0.04 | 6.52 | 0.08 | 6.94 | 0.14 | 6.97 | 0.10 | 7.00 | 0.20 |
| 13 | 6.71 | 0.09 | 7.14 | 0.20 | 7.09 | 0.15 | 6.89 | 0.11 | 6.74 | 0.06 |
| 15 | 6.59 | 0.15 | 6.69 | 0.13 | 6.76 | 0.09 | 6.69 | 0.10 | 6.68 | 0.15 |

TABLE 11

The Concentrations of Anti-lactic Acid Bacterial IgG Antibodies (unites/ml) Measured in the Serum of Cattle Vaccinated against Lactic Acid producing Bacteria (*S. bovis* and *Lactobacillus spp*) Using a Range of Different Adjuvants. The primary vaccination was during week 4 and the booster was given during week 8.

| Time | Control | | FCA | | QuilA | | Dex | | Alum | | |
|---|---|---|---|---|---|---|---|---|---|---|---|
| (weeks) | Mean | SE | Mean | SE | Mean | SE | Mean | SE | Mean | SE | P |
| IgG to *Streptococcus bovis* | | | | | | | | | | | |
| −6 | 1 | 0 | 1.0 | 0.0 | 1.6 | 0.6 | 2.5 | 1.5 | 1.0 | 0.0 | 0.60 |
| 3 | 3.8 | 1.3 | 4.2 | 0.6 | 5.0 | 1.1 | 7.1 | 2.5 | 5.4 | 0.8 | 0.53 |
| 6 | 4.8 | 1.1 | 14.4 | 2.7 | 20.4 | 3.6 | 19.4 | 2.6 | 11.4 | 3.2 | <0.01 |
| 8 | 3.1 | 1.3 | 10.1 | 1.7 | 13.7 | 2.2 | 16.6 | 1.4 | 8.4 | 1.1 | <0.01 |
| 9 | 3.3 | 1.0 | 30.4 | 16.3 | 23.9 | 2.0 | 40.8 | 8.5 | 18.8 | 3.5 | <0.01 |
| 11 | 3.3 | 1.1 | 31.2 | 19.3 | 19.1 | 2.2 | 45.4 | 10.6 | 23.3 | 7.0 | <0.01 |
| 13 | 4.7 | 0.9 | 16.9 | 6.9 | 11.1 | 1 | 29.4 | 6.7 | 9.7 | 0.4 | <0.01 |
| IgG to *Lactobacillus spp* | | | | | | | | | | | |
| −6 | 3.1 | 0.0 | 5.5 | 1.5 | 9.5 | 1.3 | 8.3 | 3.3 | 6.0 | 1.6 | 0.09 |
| 3 | 8.1 | 1.9 | 10.8 | 1.3 | 14.5 | 3.5 | 18.1 | 6.4 | 12.4 | 2.5 | 0.55 |
| 6 | 9.3 | 1.1 | 16.8 | 2.7 | 17.6 | 3.3 | 22.5 | 4.7 | 20.3 | 2.4 | <0.05 |
| 8 | 6.7 | 0.6 | 12.8 | 2.4 | 17.8 | 4.6 | 26.0 | 3.9 | 18.6 | 2.0 | <0.01 |
| 9 | 9.2 | 1.1 | 28.6 | 7.2 | 52.5 | 17.7 | 87.5 | 15.7 | 48.7 | 20.4 | <0.01 |
| 11 | 8.8 | 1.4 | 22.6 | 5.0 | 40.3 | 11.1 | 65.5 | 6.6 | 64.0 | 17.9 | <0.01 |
| 13 | 8.8 | 1.4 | 23.1 | 5.6 | 33.6 | 8.3 | 65.3 | 11.2 | 45.6 | 7.9 | <0.01 |

There were no adverse reactions to the vaccination treatments and all cattle ate consistently and gained weight throughout the experiment (Table 12). Cattle in different treatment groups gained weight at similar rates and there were no significant differences due to treatment effects.

TABLE 12

Effects of Vaccination on the Liveweight of Cattle given no Vaccination (Control) or Vaccinated against Lactic Acid Producing Bacteria using a Variety of Adjuvants. There were no significant differences between any treatment groups.

| Time | Control | | FCA | | QuilA | | Dex | | Alum | |
|---|---|---|---|---|---|---|---|---|---|---|
| (weeks) | Mean | SE | Mean | SE | Mean | SE | Mean | SE | Mean | SE |
| 2 | 323.8 | 41.6 | 306.2 | 29.4 | 289.8 | 23.4 | 310.4 | 21.0 | 305.2 | 19.7 |
| 3 | 347.0 | 47.2 | 326.0 | 32.6 | 325.3 | 33.2 | 351.5 | 8.4 | 326.0 | 20.9 |
| 4 | 340.0 | 42.8 | 319.2 | 30.3 | 302.0 | 29.7 | 326.0 | 25.6 | 316.8 | 22.0 |
| 5 | 366.5 | 44.9 | 345.6 | 37.2 | 317.2 | 32.1 | 338.0 | 29.2 | 346.0 | 22.6 |
| 6 | 364.0 | 45.0 | 341.2 | 32.2 | 317.6 | 33.9 | 342.4 | 28.1 | 342.4 | 21.7 |
| 7 | 308.5 | 44.2 | 347.2 | 33.2 | 314.0 | 35.5 | 352.2 | 27.1 | 340.6 | 21.8 |
| 8 | 386.0 | 44.9 | 361.8 | 32.6 | 341.6 | 37.9 | 368.8 | 29.8 | 364.0 | 21.5 |
| 9 | 376.5 | 45.1 | 352.4 | 31.5 | 324.8 | 38.3 | 354.0 | 30.1 | 351.2 | 23.2 |
| 10 | 402.0 | 49.8 | 375.2 | 33.4 | 348.0 | 37.0 | 380.0 | 30.8 | 374.8 | 23.0 |
| 11 | 410.5 | 48.8 | 382.8 | 32.8 | 354.8 | 38.9 | 395.2 | 32.1 | 381.2 | 24.7 |
| 12 | 419.5 | 48.3 | 393.2 | 33.5 | 370.8 | 39.9 | 401.6 | 33.7 | 392.4 | 25.8 |

Conclusions

The elevated antibody levels following vaccination with a range of adjuvants was significantly higher than in unvaccinated control animals. The fact that similar concentrations of antibodies were measured in cattle vaccinated using either DEAE-Dextran or Freund's complete/incomplete as adjuvants indicates that it is possible to achieve successful vaccination against the lactic acid producing bacteria with an adjuvant which is acceptable on grounds of animal welfare and tissue residues. This indicates that the level of antibodies produced using an adjuvant such as DEAE-Dextran in the vaccine of the present invention may provide protection against clinical acidosis in the same way as described for the vaccine prepared using Freund's complete adjuvant.

Although the animals were not challenged by treatment with high levels of fermentable carbohydrate, to initiate clinical acidosis, there were a number of changes which confirm the biological consequences of vaccination against bacteria which produce lactic acid in the gut. Significant consequences of these elevated antibody levels were seen in terms of the rumen microbial flora. The population densities in rumen fluid of both S. bovis and Lactobacillus spp were significantly reduced in animals vaccinated with QuilA and DEAE-Dextran. In addition, the pH of rumen fluid and faeces from vaccinated animals was generally higher than those of the control group. These differences were was statistically significant, but this pattern of pH change is consistent with reduction of S. bovis and Lactobacillus spp.

EXAMPLE 5

Immunisation Against Lactic Acid Bacteria in Sheep Using Various Adjuvants

An experiment was conducted to examine the efficacy of a number of different adjuvants in the preparation of vaccines against the lactic acid producing bacteria S. bovis. In Examples 1, 2 and 3 described above, evidence has been presented that vaccination using S. bovis with Freund's adjuvant or S. bovis and Lactobacillus spp with Freund's adjuvant protect the animal from the adverse effects of excessive levels of fermentable carbohydrate in the diet and the development of lactic acidosis. The experiment described below was conducted to examine the use of a range of adjuvants which would be acceptable for commercial use on the basis of animal welfare and tissue residues. A vaccine prepared with Freund's adjuvant was included in order to compare the effectiveness of the other adjuvants.

Experimental Procedures

Thirty five second-cross lambs (12 months old) were stratified for liveweight and randomly allocated to 7 treatment groups. Animals were run as a single flock under paddock conditions grazing improved phalaris/rye grass pastures. The trial was conducted during the period from November to February and with good regular rainfall during this period there was abundant green feed throughout the experiment.

The primary immunisation was administered after the animals had acclimatised to the pasture conditions. During week 6 of the experiment (4 weeks after primary immunisation) a booster injection was given. Both primary and booster vaccination was by intramuscular injection into the hind leg.

Prepation Of Vaccines

All vaccines consisted of the same bacterial preparation combined with a different adjuvant. The bacterial preparation (BP) was prepared as follows:

BP S. bovis (Sb-5) had been prepared as described above (Example 2). Each vaccine batch was prepared using 7.00 ml of $1 \times 10^{10}$ cells/ml of Sb-5 suspension.

FCA The 7.00 ml of BP was emulsified with an equal volume of Freund's complete adjuvant (Sigma) for the primary vaccination and with an equal volume of Freund's incomplete adjuvant (Sigma) for the booster. Each vaccination injection was 2 ml.

QuilA The 7.00 ml of BP was added to the Quil A (Superfos Biosector a/s) in the following way. After the 7.0 mg QuilA was dissolved in 7.00 ml sterile PBS, the BP was added to it in drops over a period of 5 minutes during vigorous mixing. The mixing was continued for another 20 minutes. Each vaccination injection was 2 ml.

Dex Dextran sulphate (Pharmacia Biotech) (43.75 mg) was mixed with 7.00 ml of sterile PBS (pH 7.4) and the BP was added to it in drops over a period of 5 minutes with vigorous mixing. The mixing was continued for another 20 minutes. Each vaccination injection was 2 ml.

Alum The 7.00 ml Sb-5 suspension was added to Inject Alum adjuvant (Pierce) in the following way: after 3.50 ml of the Alum was mixed well with 3.50 ml sterile PBS, the BP was added to it in drops over a period of minutes with vigorous mixing. The mixing was continued for another 30 minutes. Each vaccination injection was 2 ml.

Gerbu 300 μg of Gerbu Adjuvant(ScimR) was mixed with 7.00 ml sterile PBS, then the 7.00 ml of Sb-5 BP suspension was added to it in drops over a period of 5 minutes with vigorous mixing. The Mixing was continued for another 20 minutes. Each vaccination injection was 2 ml.

Samples and Measurements

Animals were weighed and samples of blood, saliva and faeces were taken immediately prior to the primary vaccination. The animals were weighed again during weeks 4, 6, 8, 11 and 12 of the experiment. Samples were taken at weekly intervals for measurement of antibody levels in blood and saliva. Samples of faeces were taken each week to measure dry matter content and pH. Animals were checked daily and observed for any signs of ill health.

Analytical Methods

The concentrations of antibodies in serum were measured using the technique described above in Example 4 with the following changes. Standard serum was a pooled sample obtained from 5 sheep in FCA group 2 weeks after booster vaccination. The conjugate was replaced by anti sheep/goat Ig (Silenus). The faecal dry matter was determined by drying faecal material to constant weight at 70° C.

Results

Table 13 summarises the concentration of antibody to *S. bovis* associated with the various vaccination treatments. By the second week following the primary vaccination, there were significantly higher levels of antibody concentrations in all groups of vaccinated animals, apart from the group given the vaccine prepared with the Gerbu adjuvant compared to the control group. Vaccination with all of the other adjuvants produced significantly ($p<0.01$) higher concentrations of antibodies than the cortrol group throughout the experiment. Freund's Complete Adjuvant produced the highest ($P<0.01$) antibody response and the response to Freund's incomplete was also higher ($p<05$) than QuiA, Dex or Alum which produced similar responses. Sheep vaccinated with Gerbu adjuvant produced lower concentrations of antibodies than with other adjuvants.

TABLE 13

Concentrations of Antibody (units/ml) in Serum of Sheep. Vaccinated Against *S. bovis* Using a Range of Different Adjuvants. Values are means and vaccines were administered during Week 2 and Week 6.

| | Con | | FCA | | FIA | | QuilA | | Dex | | Alum | | Gerbu | | |
|---|---|---|---|---|---|---|---|---|---|---|---|---|---|---|---|
| Week | Mean | SE | Mean | SE | Mean | SE | Mean | SE | Mean | SE | Mean | SE | Mean | SE | P |
| 1 | 3.2 | 1.2 | 1.2 | 0.2 | 1.2 | 0.2 | 1.6 | 0.2 | 1.2 | 0.2 | 1.6 | 0.4 | 1.4 | 0.2 | 0.12 |
| 2 | 1.8 | 0.6 | 1.8 | 0.4 | 2.0 | 0.0 | 2.0 | 0.3 | 1.8 | 0.2 | 1.8 | 0.2 | 1.6 | 0.2 | 0.9 |
| 3 | 1.8 | 0.4 | 5.8 | 1.7 | 6.8 | 3.2 | 5.4 | 1.2 | 4.1 | 1.3 | 5.6 | 1.7 | 2.9 | 1.0 | 0.2 |
| 4 | 1.2 | 0.2 | 46.6 | 13.8 | 18.2 | 5.6 | 29.2 | 18.4 | 19.8 | 8.8 | 37.4 | 9.1 | 4.5 | 2.2 | <0.0 |
| 5 | 2.4 | 0.2 | 66.4 | 16.7 | 18.8 | 7.3 | 24.8 | 13.1 | 13.6 | 6.1 | 26.8 | 6.6 | 4.5 | 1.9 | <0.0 |
| 6 | 1.2 | 0.2 | 170.0 | 77.5 | 15.6 | 5.3 | 14.8 | 7.6 | 6.8 | 3.4 | 13.2 | 4.4 | 2.0 | 1.0 | <0.0 |
| 7 | 3.0 | 0.3 | 604.6 | 102.0 | 476.8 | 225.5 | 385.8 | 72.9 | 120.3 | 41.6 | 192.4 | 57.3 | 30.4 | 7.9 | <0.0 |
| 8 | 2.4 | 0.2 | 702.2 | 142.0 | 409.4 | 99.9 | 307.0 | 34.0 | 104.8 | 35.8 | 235.2 | 73.1 | 24.2 | 6.9 | <0.0 |
| 9 | 1.6 | 0.2 | 913.6 | 144.1 | 458.6 | 161.1 | 244.2 | 36.2 | 94.1 | 37.1 | 249.4 | 67.2 | 26.3 | 8.6 | <0.0 |
| 10 | 1.0 | 0.0 | 797.8 | 94.4 | 384.0 | 75.2 | 185.6 | 29.4 | 53.5 | 21.3 | 158.2 | 33.2 | 15.1 | 4.6 | <0.0 |

Table 14 summarises the liveweight of animals in the different treatment groups throughout the experiment. There were no significant differences between sheep in any of the groups receiving different vaccinations. There are also no significant differences between the weight of sheep which received the vaccination and those in the control group.

TABLE 14

Effects of Vaccination on the Liveweights of Sheep.

| | Con | | FCA | | FIA | | QuilA | | Dex | | Alum | | Gerbu | | |
|---|---|---|---|---|---|---|---|---|---|---|---|---|---|---|---|
| Week | Mean | SE | Mean | SE | Mean | SE | Mean | SE | Mean | SE | Mean | SE | Mean | SE | P |
| 1 | 31.8 | 1.1 | 31.8 | 1.2 | 31.8 | 1.5 | 31.8 | 1.2 | 31.8 | 0.7 | 31.8 | 1.3 | 31.8 | 1.4 | 1.00 |
| 2 | 30.8 | 0.6 | 30.8 | 2.1 | 30.3 | 1.8 | 31.1 | 2.7 | 31.3 | 0.8 | 31.1 | 1.1 | 31.5 | 2.1 | 1.00 |
| 4 | 31.1 | 0.7 | 31.2 | 1.5 | 31.4 | 1.6 | 31.1 | 1.5 | 32.0 | 0.6 | 31.6 | 1.2 | 32.1 | 1.8 | 0.99 |
| 6 | 32.7 | 0.7 | 33.1 | 1.5 | 32.2 | 2.0 | 33.0 | 1.7 | 33.1 | 0.6 | 33.2 | 1.2 | 33.0 | 1.5 | 1.00 |
| 8 | 32.8 | 0.7 | 32.2 | 1.4 | 33.0 | 2.1 | 31.3 | 1.5 | 32.8 | 0.8 | 32.9 | 1.4 | 32.8 | 1.7 | 0.98 |
| 11 | 33.5 | 1.0 | 33.8 | 1.6 | 34.1 | 1.8 | 32.8 | 1.5 | 34.2 | 0.5 | 32.8 | 1.3 | 34.0 | 1.9 | 0.99 |
| 12 | 32.7 | 1.0 | 32.9 | 1.6 | 32.6 | 2.1 | 32.4 | 1.5 | 32.9 | 0.7 | 33.1 | 1.2 | 33.6 | 1.8 | 1.00 |

TABLE 15

Faecal Dry Matter of Sheep Grazing Green Summer Pasture.

| Time | Control | | FCA | | FIA | | QuilA | | Dex | | Alum | | Gerbu | | |
|---|---|---|---|---|---|---|---|---|---|---|---|---|---|---|---|
| wks | Mean | SE | Mean | SE | Mean | SE | Mean | SE | Mean | SE | Mean | SE | Mean | SE | P |
| 1 | 24.4 | 0.9 | 24.6 | 2.5 | 21.9 | 1.9 | 24.4 | 1.3 | 23 | 1.2 | 24.4 | 0.6 | 27.4 | 1.5 | 0.33 |
| 3 | 22.3 | 4.1 | 25.5 | 2.4 | 22.8 | 2.2 | 21.9 | 3.9 | 24.3 | 2 | 25.5 | 1.4 | 32.7 | 4 | 0.22 |
| 4 | 22.1 | 1.1 | 22.4 | 2 | 20.7 | 1.5 | 20.9 | 1.2 | 22.9 | 2.1 | 22.8 | 1.8 | 23 | 1.2 | 0.91 |
| 5 | 29.1 | 1.7 | 23.0 | 2.2 | 22.7 | 1.1 | 26.7 | 5.9 | 26.5 | 1.4 | 27.9 | 4.8 | 26.5 | 1.4 | 0.75 |
| 6 | 27.7 | 0.6 | 27.2 | 3.6 | 20.5 | 2.3 | 27.7 | 2.4 | 30.1 | 2.5 | 26.7 | 2.6 | 31.2 | 4.2 | 0.23 |
| 7 | 29.8 | 2.3 | 34.4 | 2.7 | 27.4 | 2.0 | 38.6 | 1.8 | 31.3 | 1.9 | 29.5 | 2.2 | 31.4 | 2.5 | 0.03 |

Sheep were either given no vaccination or were vaccinated against lactic acid producing bacteria with a range of adjuvants with a primary injection during week 2 and a booster during week 6. The faecal dry matter is summarised in Table 15. In week 7 the faecal dry matter content of sheep vaccinated against S. bovis using FCA or QuilA were higher ($P<0.05$) than in the control group.

Conclusions

The results of this experiment show that a number of adjuvants which are well recognised for regular use are effective in increasing and maintaining high levels of antibodies against lactic acid producing bacteria in the gut. The biological benefits of the immune response against S. bovis are seen in this experiment even in the absence of an acute challenge with carbohydrate. Green grass can have high levels of soluble carbohydrate as sugars build up during photosynthesis. These sugars can pass undigested to the hind gut where fermentation can lead to some accumulation of lactic acid. Lactic acid is an osmotically active molecule and its presence, even in low concentrations can result in higher water content in the faeces. The increased dry matter content of the sheep vaccinated against S. bovis is therefore important as it suggests a subtle, yet significant effect on acid accumulation in the hind gut.

EXAMPLE 6

Vaccination Against S. bovis and Lactobacillus spp in the Horse

Previous examples have described the invention in terms of the effect of vaccination against lactic producing bacteria in ruminant species. The example described below was conducted to investigate the effect of vaccination in the horse which is an example of a monogastric animal. Monogastric animals differ from ruminants in that the food enters an acid stomach from the oesophagus rather than the reticulo—rumen which is a large fermentation compartment. In the horse, feed is digested in the stomach and there is absorption in the small intestine followed by fermentation in the hind gut. It is possible for starch and sugars to pass undigested to the hind gut and for rapid fermentation to lead to the accumulation of acids. Acidic conditions in the hind gut can lead to a number of serious disease conditions such as laminitis. In very serious cases death can result from systemic acidosis. The horse has a large hind gut with extensive fermentation and is therefore an excellent example for studying vaccination against lactic acid producing bacteria in monogastric species.

Experimental Procedures

Six horses were used in an experiment to examine antibody responses in horses immunised against lactic acid producing bacteria. Three horses were assigned to each of two treatment groups. The control group received no vaccination while the immunised group received vaccination treatment based on Freund's Complete Adjuvant CFCA) for the primary injection and Freund's Incomplete Adjuvant (FIA) for the booster and a mixture of S. bovis and Lactobacillus spp. The vaccines were prepared by mixing 19 ml of $1 \times 10^{10}$ Sb-5 ml and 7 ml of $2 \times 10_{10}$ LB/ml (isolated and prepared as previously described (examples 1 & 4). This mixture was centrifuged at 4° C., 10.000 g for 20 minutes. Following centrifugation. 16 ml of the supernatant was discarded. The bacteria unare resuspended by vigorous mixing for 5 minutes. Five ml of the vaccine suspension were emulsified with 5 ml Freund's complete adjuvant for the primary immunisation. The remaining 5 ml of the suspension was stored at −80° C. for use in preparing the booster injection. This was prepared by first thawing the 5 ml suspension and then emulsifying it with 5 ml Freund's incomplete adjuvant.

The primary vaccination was given 4 weeks after animals had adapted to pasture conditions for the experiment. The second booster immunisation was given 4 weeks after the primary injection. Samples of blood, saliva and faeces were taken at the time of the primary immunisation, 4 weeks later prior to the booster injection and again 2 weeks after the booster injection.

Results

Table 16 summarises the antibody concentrations (IgG) measured in serum samples. The data were analysed following log transformation using standard analysis of variance. There was a significant increase in the concentrations of IgG to *S. bovis* and to Lactobacillus spp measured in the samples taken two weeks following the booster injection.

TABLE 16

Concentration (units/ml) of Anti-lactic Acid Bacteria Antibody IgG in Serum Samples in the Horse.

| Time | Control | | Immunisation | | |
|---|---|---|---|---|---|
| (Weeks) | Mean | SE | Mean | SE | P |
| IgG to *S. bovis* | | | | | |
| Primary injection | 92.3 | 6.7 | 87.3 | 7.0 | 0.53 |
| Booster injection | 94.3 | 10.3 | 106.3 | 15.8 | 0.58 |
| 2 weeks post booster | 94.7 | 10.7 | 187.3 | 21.4 | <0.05 |
| IgG to Lactobacillus spp | | | | | |
| Primary injection | 35.3 | 2.3 | 31.7 | 0.9 | 0.22 |
| Booster injection | 36.3 | 5.6 | 57.3 | 9.3 | 0.12 |
| 2 weeks post booster | 33.3 | 2.3 | 104.0 | 14.7 | <0.01 |

Table 17 summarises the effect of vaccination on faecal pH. Although the faecal pH of the immunised group was, higher in the vaccinated group compared to the control group this difference was not statically significant (P=0.08).

TABLE 17

Effect of Vaccination on the Faecal pH in the Horse.

| Time | Control | | Immunisation | |
|---|---|---|---|---|
| (weeks) | Mean | SE | Mean | SE |
| 1 | 6.86 | 0.21 | 6.71 | 0.38 |
| 5 | 6.98 | 0.10 | 7.04 | 0.13 |
| 7 | 6.90 | 0.18 | 7.24 | 0.08 |

Conclusions

The results show that it is possible to vaccinate the horse against the major lactic acid producing organisms *S. bovis* and Lactobacillus spp. It is interesting that the antibody concentrations in the control (unvaccinated horses) were higher than measured in sheep and cattle. It is possible that some natural immunity develops in the horse. This is probably associated with the common practice of coprophagy when animals are fed diets high in sugars or starch which cause an acidic pattern of fermentation in the hind gut. It is clear that this natural immunity, if it occurs, can be further enhanced through vaccination. The biological consequence of this antibody response was seen in slightly higher faecal pH in the animals which were vaccinated. These horses were not challenged with grain and although grazing green pasture it is not likely that they would have been consuming abnormally high levels of readily fermentable carbohydrate.

Protection against acidosis in the hind gut of horses is extremely important in terms of preventing against disorders such as founder or laminitis. The fact that vaccination is effective in raising antibodies to *S. bovis* and Lactobacillus spp in the horse indicates that the same technique will be of benefit in other monogastric species such as dogs, rabbits, pigs and poultry.

The present inventors have obtained results that demonstrate that animals when administered an effective amount of a vaccine comprising an acid producing microorganism can be protected from the over production of acid. In particular, the vaccine of the invention can protect ruminants from acidosis.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of preventing overproduction of acid in the intestinal tract of an animal comprising administering to the animal, in an amount effective to prevent overproduction of acid in the intestinal tract, a vaccine including *Streptococcus bovis* species, wherein the *Streptococcus bovis* is strain Sb-5 (N94/8255), so as to elicit an immune response in the animal effective to prevent the overproduction of acid in the intestinal tract.

2. The method according to claim 1 wherein the animal is selected from the group of ruminant animals consisting of sheep, cattle, goats and camelids and from the group of monogastric animals consisting of horses, pigs, poultry and humans.

3. The method according to claim 1 wherein the over production of acid causes a condition in the animal selected from the group consisting of acidosis, lactic acidosis, grain engorgement, grain overload, carbohydrate overload, founder, laminitis, and acute indigestion.

4. The method according to claim 1 wherein the vaccine is administered by the route selected from the group consisting of subcutaneous, intramuscular, and interperitoneal.

5. A vaccine which elicits an immune response in an animal effective to prevent over production of acid in the intestinal tract of the animal, the vaccine comprising *Streptococcus bovis*, wherein the *Streptococcus bovis* is strain Sb-5 (N94/8255), and a pharmaceutically acceptable excipient or carrier.

6. The vaccine according, to claim 5 comprising live cells, attenuated cells, killed whole cells, or cell lysatel, of *Streptococcus bovis*.

7. The vaccine according to claim 5 further including a pharmaceutically acceptable adjuvant, carrier or excipient.

8. An isolated microorganism *Streptococcus bovis* designated strain Sb-5 (N94/8255).

\* \* \* \* \*